United States Patent

Briggs et al.

[11] Patent Number: 4,927,945
[45] Date of Patent: May 22, 1990

[54] PROCESS FOR PREPARING DIPHENYL ETHERS

[75] Inventors: Stuart P. Briggs, Faversham; Derek A. Wood, Sittingbourne, both of England

[73] Assignee: Shell Internationale Research Maatschappij, B.V., The Hague, Netherlands

[21] Appl. No.: 230,104

[22] Filed: Aug. 9, 1988

[30] Foreign Application Priority Data

Sep. 1, 1987 [GB] United Kingdom ............. 8720511

[51] Int. Cl.$^5$ ........................................... C07D 307/00
[52] U.S. Cl. ..................................... 549/305; 549/304
[58] Field of Search ................................ 549/304, 305

[56] References Cited

FOREIGN PATENT DOCUMENTS 145078  6/1985  European Pat. Off. ............ 549/305
219144  4/1987  European Pat. Off. ............ 549/305
2182328 5/1987  United Kingdom .............. 549/305

*Primary Examiner*—Mary C. Lee
*Assistant Examiner*—J. Richter

[57] ABSTRACT

Diphenyl ether derivatives of formula II

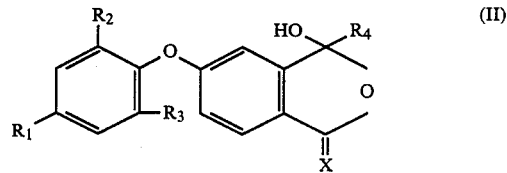

wherein $R_1$ represents a hydrogen or halogen atom or an alkyl or haloalkyl group, $R_2$ and $R_3$, which may be the same or different, each independently represents a hydrogen or halogen atom, or an alkyl, haloalkyl, nitro or cyano group, $R_4$ represents an alkyl group and X represents an oxygen or sulphur atom, useful as intermediates in the preparation of diphenyl ether herbicides, are prepared by treating a compound of formula III

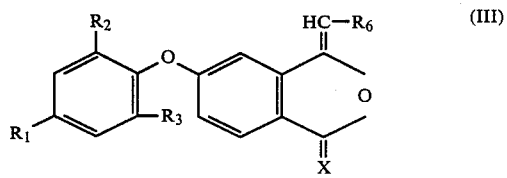

where $R_1$, $R_2$, $R_3$ and X are as defined above and $R_6$ is a hydrogen atom or an alkyl group, with an alkali under hydrolyzing conditions.

14 Claims, No Drawings

PROCESS FOR PREPARING DIPHENYL ETHERS

This invention relates to a process for preparing diphenyl ether derivatives and the use of such derivatives as intermediates in the preparation of certain diphenyl ether herbicides.

The applicants' copending UK Patent Application No. 8720509 corresponding to U.S. patent application Ser. No. 07/230,099, filed Aug. 9, 1988 describes and claims herbicidal phenoxy phthalide derivatives having the general formula I:

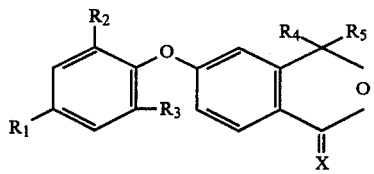

wherein $R_1$ represents a hydrogen or halogen atom, preferably chlorine, or an alkyl or haloalkyl group, suitably of 1–4 carbon atoms, preferably trifluoromethyl; $R_2$ and $R_3$, which may be the same or different, each independently represents a hydrogen or halogen atom, preferably chlorine, or an alkyl or haloalkyl group, suitably of 1–4 carbon atoms, for example trifluoromethyl, or a nitro or cyano group; $R_4$ represents a saturated alkyl group; $R_5$ represents an unsaturated alkyl group; and X represents an oxygen or sulphur atom.

The applicants' copending European Patent Application Publication No. 219144 similarly describes and claims herbicidal phenoxy phthalide derivatives having the formula (1) above where X is oxygen and $R_4$ and $R_5$, which may be the same or different, each independently represents an alkyl group.

The synthesis of such derivatives, especially where $R_4$ and $R_5$ are not identical, can be complex. Thus for example, in accordance with the above mentioned EP-A-219144, the synthesis of a compound when $R_4$ is methyl and $R_5$ is ethyl is carried out by first reacting the corresponding 3-hydroxy phthalide (ie. a compound of formula I where $R_4$ is hydrogen and $R_5$ is hydroxy) with a Grignard reagent (eg. methyl magnesium bromide) to give the 3-methyl phthalide and then reacting the product with an alkyl halide (eg. iodoethane) in the presence of n-butyl lithium to give the desired 3-methyl, 3-ethyl phthalide.

According to the present invention we provide a process for the preparation of a diphenyl ether derivative of formula II

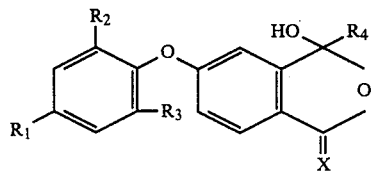

wherein $R_1$ represents a hydrogen or halogen atom, preferably chlorine, or an alkyl or haloalkyl group, suitably of 1–4 carbon atoms, preferably trifluoromethyl; $R_2$ and $R_3$, which may be the same or different, each independently represents a hydrogen or halogen atom, preferably chlorine, or an alkyl or haloalkyl group, suitably of 1–4 carbon atoms, for example trifluoromethyl, or a nitro or cyano group; $R_4$ represents an alkyl group, preferably having up to 4 carbon atoms, preferably methyl or ethyl; and X represents an oxygen or sulphur atom, comprising treating a compound of formula III

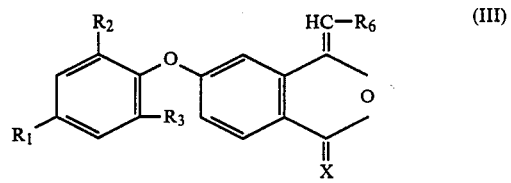

where $R_1$, $R_2$, $R_3$ and X are as defined above and $R_6$ is a hydrogen atom or an alkyl group, preferably having up to 3 carbon atoms and is preferably a hydrogen atom or a methyl group, with an alkali under hydrolysing conditions.

The alkali is suitably potassium or sodium hydroxide, although other alkali metal hydroxides such as lithium hydroxide or caesium hydroxide may be employed. The reaction preferably employs an excess of alkali, suitably 1 to 2 moles of alkali per mole of compound III. The reaction is suitably carried out in aqueous solution or in a mixed solution of water and a compatible solvent such as an alcohol (eg. ethanol or isopropanol), dioxan, or tetrahydrofuran. The amount of non aqueous solvent is not critical but in general the ratio of aqueous/non aqueous solvent is in the range (by volume) of 1:1 to 1:30.

The alkaline hydrolysis may be carried out at ambient temperature or elevated temperatures, for example up to the refluxing temperature of the solvent system, although the reaction is usually carried out at temperatures up to 60° C.

According to a further aspect of the present invention the compounds of formula III where X is an oxygen atom are prepared by reacting a compound of formula IV

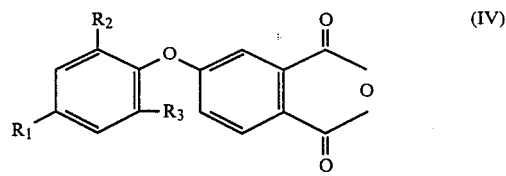

where $R_1$, $R_2$ and $R_3$ are as defined above, with an acid anhydride of formula $(R_6CH_2CO)_2O$, where $R_6$ is as defined above, under substantially anhydrous conditions in the presence of a metal salt of an organic acid or an organic base. Suitable metal salts are for example sodium or potassium salts of acetic or propionic acid. Suitable organic bases include triethylamine and tributylamine.

The reaction is suitably effected under normal pressure at elevated temperature of for example 100° 1 to 200° C. Preferably an excess of anhydride is employed.

It is not always necessary to isolate the compound of formula 111 before proceeding with alkaline hydrolysis to compounds of formula II.

However the reaction may be followed by any necessary separation procedures such as chromatography and/or recrystallisation from toluene to remove unwanted isomeric bi-products due to reaction with the second carbonyl group of the anhydride IV. However in practice it has usually been found that the desired compound of formula III is obtained as the major product.

The anhydrides of formula IV are known for example from U.S. Pat. No. 4 334 915.

They may be prepared for example by reaction of 3,4-dimethylphenol with a substituted halobenzene followed by oxidation of the methyl groups to acid groups and ring closure to form the anhydride of formula IV.

The invention also includes compounds of formula II when prepared by the process described above.

Compounds of formula II above are valuable intermediates for the preparation of compounds of formula I. Their use in the preparation of compounds of formula I where $R_4$ represents a saturated alkyl group and $R_5$ represents an unsaturated alkyl group is described and claimed in our copending UK Patent Application No. 8720509. They are however also valuable in the preparation of compounds of formula I where $R_4$ and $R_5$, which may be the same or different, each independently represents an alkyl group.

Thus according to a further aspect of this invention we provide a process for the preparation of a compound of formula I where $R_4$ and $R_5$, which may be the same or different, each independently represents an alkyl group comprising reacting a compound of formula II which has been prepared as described above with an organometallic compound of formula $R_5$—M—Hal where M represents a metal atom and Hal represents a halogen atom.

The moiety Hal may be a chlorine, bromine or iodine atom.

The organometallic reagent used is preferably an organomagnesium compound (Grignard reagent), which may be prepared according to established procedures, e.g. by taking up the appropriate alkyl halide and magnesium metal in an aliphatic ether, such as diethyl ether in the absence of water. The reaction of the compound of formula II with that Grignard reagent is suitably carried out in a solvent, which may also be diethyl ether, or may be a different inert organic solvent such as tetrahydrofuran. The formation of the Grignard reagent and its reaction with the compound of formula II are each suitably carried out at ambient temperatures, although temperatures up to the boiling point of the solvent used may be employed. The Grignard organomagnesium complex may be supplemented by the generation of an organocadmium complex through the addition of cadmium chloride.

The invention also includes compounds of formula I when prepared by the process defined above.

Preferably in the compound of formula I, $R_1$ is trifluoromethyl, $R_2$ is a chlorine atom, $R_3$ is hydrogen, X is oxygen, one of $R_4$ and $R_5$ is a methyl group and the other is an ethyl group.

The invention is illustrated in the following Examples.

EXAMPLE 1

5-(2-chloro-4-trifluoromethylphenoxy)-phthalic anhydride (a) Sodium hydroxide (740 g, 18.5 mol), 3,4-dimethylphenol (2255 g, 18.5 mol) and sulpholane (7.51) were mixed and stirred at room temperature for 1 hour. Petroleum ether b.p. 100°–120° C. (21) was added and the mixture heated to reflux and water removed by azeotropic distillation. After 7 hours further sodium hydroxide (74 g, 1.85 mol) was added and refluxing continued until water ceased distilling over. 3-chloro-4-fluorobenzotrifluoride (3672 g, 18.5 mol) was added at 80°–90° C. After completion of the reaction and cooling, the reaction mixture was poured into cold water and the organic layer separated. After washing with sodium hydroxide and water the organic phase was concentrated to yield an oil (5178 g.) distilling at 0.2mm Hg/1120° C.

(b) The product of step (a) (300.5 g 1.0 mol) in acetic acid (600 ml) and acetic anhydride (26 ml) was mixed with cobalt acetate (9 g, 0.036 mol) and cobalt bromide (6 g, 0.018 mol). The mixture was stirred, heated to 100° C. and oxygen passed through at about 2 l.min$^{-1}$. After the exothermic reaction subsided, solvent was removed by distillation and the residue triturated with toluene to give a white solid (239 g) m.p. 170°–170° C.

(c) Product obtained as in step b (730 g, 2.03 mol) in xylene (2.51) was heated under reflux and water removed by azeotropic distillation. After 6 hours reflux the mixture was cooled, filtered and xylene removed by distillation to give a yellow oil which crystallised from petroluem spirit.

Yield of the title compound 624 g. m.p. 88°–91° C.

EXAMPLE 2

5-(2-chloro-4-trifluoromethylphenoxy)-3-methylmethylene-1-(3H isobenzofuranone

Sodium propionate (11.52 g, 0.12 mol), propionic anhydride (52 g, 0.4 mol) and 5-(2-chloro-4-trifluoromethyl- phenoxy)-phthalic anhydride (68.5 g, 0.2 mol), were mixed together and heated for 90 hours at 150° C. under a nitrogen atmosphere. Unreacted propionic anhydride was distilled from the reaction mixture at reduced pressure. The residue Was partitioned between toluene and water, then the dried organic phase stripped to afford a red oil. Toluene (70 ml) was added to the red oil and the resultant solution left overnight to crystallise. Off-white crystals of the product were collected by filtration and washed with a small quantity of toluene (m.p. 144.5° to 146.5° C.).

Yield=29.5 g (41.4%)

Analysis: Calculated: C 57.5; H 2.8;

Found: C 57.8; H 2.9.

EXAMPLE 3

5-(2-chloro-trifluoromethylphenoxy)-3-ethyl-3-hydroxyphthalide

Potassium hydroxide (10.08 g, 0.18 mol) was dissolved in water (15 ml) and added to a stirred slurry of the product of Example 2 (31.02 g, 90mmol) in ethanol (100 ml). Within 5 min the solid had dissolved forming a brown solution. After 1 hour, water (150 ml) Was added and the solution acidified with concentrated hydrochloric acid, then extracted with ethyl acetate (3×100 ml). The combined extracts were dried (MgSO$_4$) and concentrated to afford an oil which crystallised from 5% (by vol.) diethyl ether in 40°–60° C. b.p. petroleum ether (50 ml) giving the hydroxy ethyl phthalide product as a white solid (m.p. 122°–124° C.).

Yield=32.6 g (100%)

Analysis: Calculated: C 54.78; H 3.25;

Found: C 54.S ; H 3.2.

EXAMPLE 4

5-(2-chloro-4-trifluoromethylphenoxy)-3-ethyl-3-methyl-phthalide

Magnesium (6.5 g, 0.268 mol) was slurried in diethylether (250 ml) under nitrogen atmosphere and treated with iodomethane (38.1 g, 0.268 mol) to form the Grignard reagent, methyl magnesium iodide. The phthalide prepared in Example 3 dissolved in diethylether (250 ml) and tetrahydrofuran (150 ml) was run into the Grignard reagent over 30 mins. maintaining a steady reflux. After heating for a further 30 mins., the reaction mixture was poured into dilute $H_2SO_4$/ice (2 l), the organic phase was separated and the aqueous phase extracted with ethyl acetate (3×200 ml). The combined organic extracts were washed with water (2×150 ml), filtered through a silica pad, stripped to afford a brown oil, then cleaned on a silica column (500 g) by elution with 20% ethyl acetate: 80% petroleum ether. The eluent containing the major product was stripped to afford the ethyl methylphthalide product as an oil.

Yield=23.9 g (96%).
Analysis: Calculated: C 58.3; H 3.8;
Found: C 58.5; H 4.0.

EXAMPLE 5

5-(2-chloro-4-trifluoromethylphenoxy)-3-methyl-3-hydroxyphthalide

A mixture of 5-(2-chloro-4-trifluoromethylphenoxy)phthalic anhydride (34.25 g, 0.1 mol), potassium acetate (9.8 g, 0.1 mol) and acetic anhydride (50 ml) was stirred and heated in an oil-bath at 130° C. for 15 hours. Excess acetic anhydride was distilled off under reduced pressure and after cooling the residue was dissolved in ethanol (400 ml). This solution was stirred overnight with potassium hydroxide (28 g, 0.5 mol) dissolved in water (30 ml). After removal of the ethanol under reduced pressure, the residue was portioned between water and ether. The aqueous layer was extracted twice more with fresh ether and then acidified with concentrated hydrochloric acid HCl. The crude product was extracted with ethyl acetate to give a brown viscous oil (18.8 g). Purification by column chromatography gave a pure isomer which solidified on standing, m.p.=100°-103° C.

Analysis: Calculated: C 53.58; H 2.81;
Found: C 53.7; H 2.8.

We claim:

1. A process for the preparation of a diphenyl ether derivative of formula II.

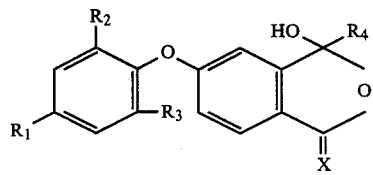

wherein $R_1$ represents a hydrogen or halogen atom or an alkyl or haloalkyl group, $R_2$ and $R_3$, which may be the same or different, each independently represents a hydrogen or halogen atom, or an alkyl, haloalkyl, nitro or cyano group, $R_4$ represents and alkyl group and X represents an oxygen or sulphur atom, comprising hydrolysing a compound of formula III

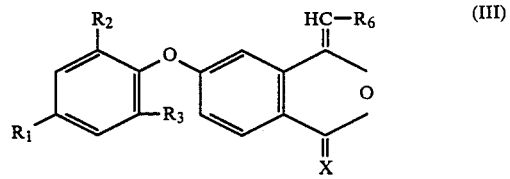

where $R_1$, $R_2$, $R_3$ and X are as defined above and $R_6$ is a hydrogen atom or an alkyl group, with an alkali metal hydroxide under hydrolysing conditions, said hydrolysis step being undertaken in aqueous solution at a temperature ranging from ambient to the refluxing temperature of said solution.

2. A process according to claim 1 wherein $R_1$ is $CF_3$, $R_2$ is chlorine and $R_3$ is hydrogen.

3. A process according to claim 1 or 2 wherein $R_6$ is a hydrogen atom or a methyl group.

4. A process according to claim 1 or 2 wherein X is oxygen.

5. A process according to claim 1 or 2 wherein the alkali metal hydroxide is sodium or potassium hydroxide.

6. A process according to claim 1 or 2 wherein the compound of formula III where X is an oxygen atom is prepared by reacting a compound of formula IV

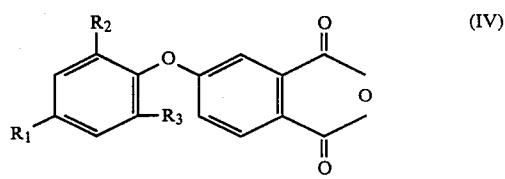

where $R_1$, $R_2$ and $R_3$ are as in claim 1, with an acid anhydride of formula $(R_6CH_2CO)_2O$, where $R_6$ is as defined in claim 1, under substantially anhydrous conditions in the presence of a metal salt of an organic acid or an organic base and optionally converting the compound of formula III where X is an oxygen atom to a compound of formula III where X is a sulphur atom.

7. A process according to claim 6 wherein the acid anhydride is acetic anhydride or propionic anhydride.

8. A process according to claim 6 wherein the reaction with an acid anhydride is carried out in the presence of the sodium or potassium salt of acetic or propionic acid.

9. A process for the preparation of a compound of formula I

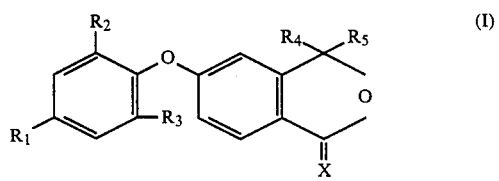

where $R_1$, $R_2$, $R_3$ and X are as defined in claim 1 and $R_4$ and $R_5$, which may be the same or different, each independently represents an alkyl group, comprising reacting a compound of formula II which has been prepared according to claim 1 with an organometallic compound of formula $R_5$—M—Hal where M represents a metal atom and Hal represents a halogen atom.

10. A process according to claim 9 wherein the organometallic compound is an organo-magnesium compound.

11. A process according to claim 9 or 10 wherein $R_1$ is trifluoromethyl, $R_2$ is a chlorine atom, $R_3$ is hydrogen, X is oxygen, one of $R_4$ and $R_5$ is a methyl group and the other is an ethyl group.

12. A process according to claim 1 wherein said hydrolysis step is undertaken at a temperature ranging from ambient to 60° C.

13. A process according to claim 1 wherein said hydrolysis step is undertaken in an aqueous solution of water and a compatible solvent selected from the group consisting of alcohol, dioxan or tetrahydrofuran.

14. A process according to claim 13 wherein the ratio of water to said compatible solvent ranges from 1:1 to 1:30.

* * * * *